(12) United States Patent
Madeira

(10) Patent No.: US 10,675,456 B2
(45) Date of Patent: Jun. 9, 2020

(54) SYSTEM AND METHODS FOR PERCUTANEOUS MECHANICAL AND/OR NEURAL INTERFACE

(71) Applicant: Robert Madeira, Allentown, PA (US)

(72) Inventor: Robert Madeira, Allentown, PA (US)

( * ) Notice: Subject to any disclaimer, the term of this patent is extended or adjusted under 35 U.S.C. 154(b) by 106 days.

(21) Appl. No.: 15/707,185

(22) Filed: Sep. 18, 2017

(65) Prior Publication Data

US 2018/0078757 A1    Mar. 22, 2018

Related U.S. Application Data

(60) Provisional application No. 62/495,625, filed on Sep. 20, 2016.

(51) Int. Cl.
| | |
|---|---|
| *A61F 2/78* | (2006.01) |
| *A61N 1/05* | (2006.01) |
| *A61N 1/36* | (2006.01) |
| *A61N 1/18* | (2006.01) |
| *A61F 2/38* | (2006.01) |

(Continued)

(52) U.S. Cl.
CPC ........ *A61N 1/0551* (2013.01); *A61B 5/04001* (2013.01); *A61B 5/685* (2013.01); *A61B 5/6877* (2013.01); *A61B 5/6884* (2013.01); *A61F 2/0063* (2013.01); *A61F 2/02* (2013.01); *A61F 2/0811* (2013.01); *A61F 2/30907* (2013.01); *A61F 2/389* (2013.01); *A61F 2/3859* (2013.01); *A61F 2/60* (2013.01); *A61N 1/18* (2013.01); *A61N 1/36003* (2013.01); *A61F 2002/0068* (2013.01); *A61F 2002/087* (2013.01); *A61F 2002/0823* (2013.01); *A61F 2002/0852* (2013.01); *A61F 2002/2825* (2013.01); *A61F 2002/30602* (2013.01); *A61F 2002/30607* (2013.01); *A61F 2002/30884* (2013.01); *A61F 2002/3881* (2013.01); *A61F 2002/607* (2013.01); *A61F 2002/608* (2013.01); *A61F 2002/7881* (2013.01); *A61F 2002/7887* (2013.01); *A61N 1/0558* (2013.01); *A61N 1/36057* (2013.01)

(58) Field of Classification Search
CPC .. A61F 2/78; A61F 2/38; A61F 2/2326; A61F 2/3662; A61F 2/24; A61F 2002/7887; A61F 2002/2825; A61F 2002/30154; A61F 2002/30329; A61F 2002/30339
USPC ................................. 623/23.26, 38
See application file for complete search history.

(56) References Cited

U.S. PATENT DOCUMENTS

| | | | |
|---|---|---|---|
| 7,083,648 B2 * | 8/2006 | Yu .............................. | A61F 2/60 604/174 |
| 2004/0172138 A1 * | 9/2004 | May ..................... | A61B 17/164 623/20.36 |

(Continued)

*Primary Examiner* — Bruce E Snow

(57) ABSTRACT

A system and method for improving limb function through the use of percutaneous mechanical and neural interfaces. The system generally uses a hollow long bone axial rod that is inserted into the long bone medullary cavity. A transfer rod with a central channel is mounted to the long bone axial rod. An exterior body attachment is connected to the transfer rod and attachment rings attach muscle groups, fascia layers and dermal layers to the transfer rod. Additionally, the system is configured to collect and transmit nerve signaling data to an external processor and additionally configured to transmit data from the external processor to the plurality of nerves.

16 Claims, 9 Drawing Sheets

(51) Int. Cl.
  *A61F 2/60* (2006.01)
  *A61F 2/08* (2006.01)
  *A61F 2/30* (2006.01)
  *A61F 2/00* (2006.01)
  *A61F 2/02* (2006.01)
  *A61B 5/04* (2006.01)
  *A61B 5/00* (2006.01)
  *A61F 2/28* (2006.01)

(56) References Cited

U.S. PATENT DOCUMENTS

| | | | |
|---|---|---|---|
| 2006/0095140 A1* | 5/2006 | Steinbarger | A61F 2/76 623/38 |
| 2015/0265430 A1* | 9/2015 | Branemark | A61F 2/2814 623/32 |
| 2016/0151174 A1* | 6/2016 | Radzinsky | A61F 2/76 623/38 |
| 2019/0053920 A1* | 2/2019 | Armitage | A61F 2/54 |

* cited by examiner

SYSTEM AND METHODS FOR PERCUTANEOUS MECHANICAL AND/OR NEURAL INTERFACE

RELATED APPLICATIONS

This application claims priority to U.S. Provisional Application No. 62/495,625 filed Sep. 20, 2016. The entire contents of the above application are hereby incorporated by reference as though fully set forth herein.

FIELD

The present invention relates to the field of human-machine interfaces. More specifically, the present invention relates to mechanical-neuro connection systems for attachment of objects to the body.

BACKGROUND

Amputation is the removal of a limb by trauma, medical illness, or surgery. A prosthetic is an artificial device that replaces an amputated or otherwise missing body part, which may be amputated or lost through trauma, disease, or congenital conditions. There are several ways a prosthesis can be attached to a stump. It may be held on with suction, a locking pin, or with a harness. Each method has advantages and drawbacks. A harness can be bulky and not move as well as the other systems. A locking pin may cause irritation where it contacts the stump. Suction is generally considered the best choice, but the user must put the prosthesis on accurately in order to get secure suction.

These methods are not conducive to use of a variety of exterior attachments other than prosthetic devices, such as a tool, for example. Nor are they able to capture and utilize nervous system signaling in any meaningful fashion. Thus, it would be useful to have a new system and method to improve limb function after amputation that also allows a significantly higher degree of human-machine interface.

BRIEF SUMMARY OF THE INVENTION

It is the object of the present invention to provide a new system and method for improving limb function through the use of mechanical and percutaneous neural interfaces. One embodiment of the present invention is system for attachment of a device to a bone. It is comprised generally of a hollow long bone axial rod inserted into the long bone medullary cavity; a transfer rod with a central channel mounted to the long bone axial rod; an exterior body attachment connected to the transfer rod at the end opposite the long bone axial rod; and attachment rings for attaching muscle groups, fascia layers and dermal layers to the transfer rod. Additionally, this embodiment of the present invention may include a system configured to collect and transmit nerve signaling data to an external processor and additionally configured to transmit data from the external processor to the nerves.

In a second embodiment of the present invention, a system for attachment of a device in a transverse direction to a bone is disclosed. It is comprised generally of a central bone implant; a subcutaneous central mount with a central channel that can be viewed from the top of the skin that is inserted and secured into the central bone implant; a stud connector locked into the central mount; and a spring for pressure loading the central mount in a locked position.

A third embodiment of the present invention is a system for attachment of a device to a bone. It is comprised generally of a device with female socket connectors at one end; a hollow long bone axial rod that inserts into a long bone medullary cavity; and a transfer rod mounted to long bone axial rod with at matching male ratchet connectors separated by a central rod portion. The male ratchet connectors are inserted into the female socket connectors using a ratchet retention spring ball system.

DETAILED DESCRIPTION

Figure 1:
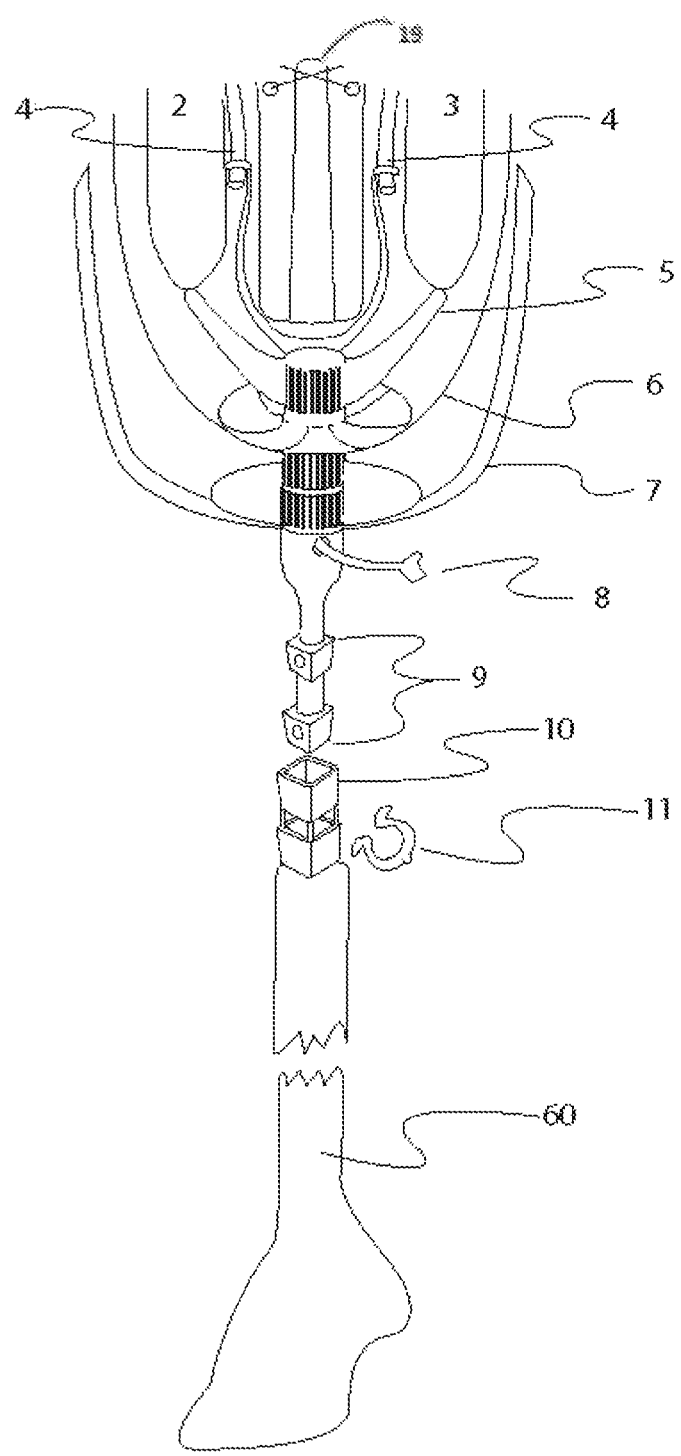
FIG. 1 is front view of an embodiment of the present invention.

Turning to FIG. 1, a summary view of an embodiment of the present invention is shown with the following general components: a first muscle group 2, second muscle group 3, nerve attachment clips 4, muscular attachment ring 5, fascia attachment ring 6, dermal/epidermal attachment ring 7, nerve signal processor attachment connector 8, prosthetic rod attachment ratchet (male) 9, prosthetic device attachment socket (female) 10, prosthetic attachment retention clip 11. Part 60 represents any compatible prosthetic attachment.

Figure 2:
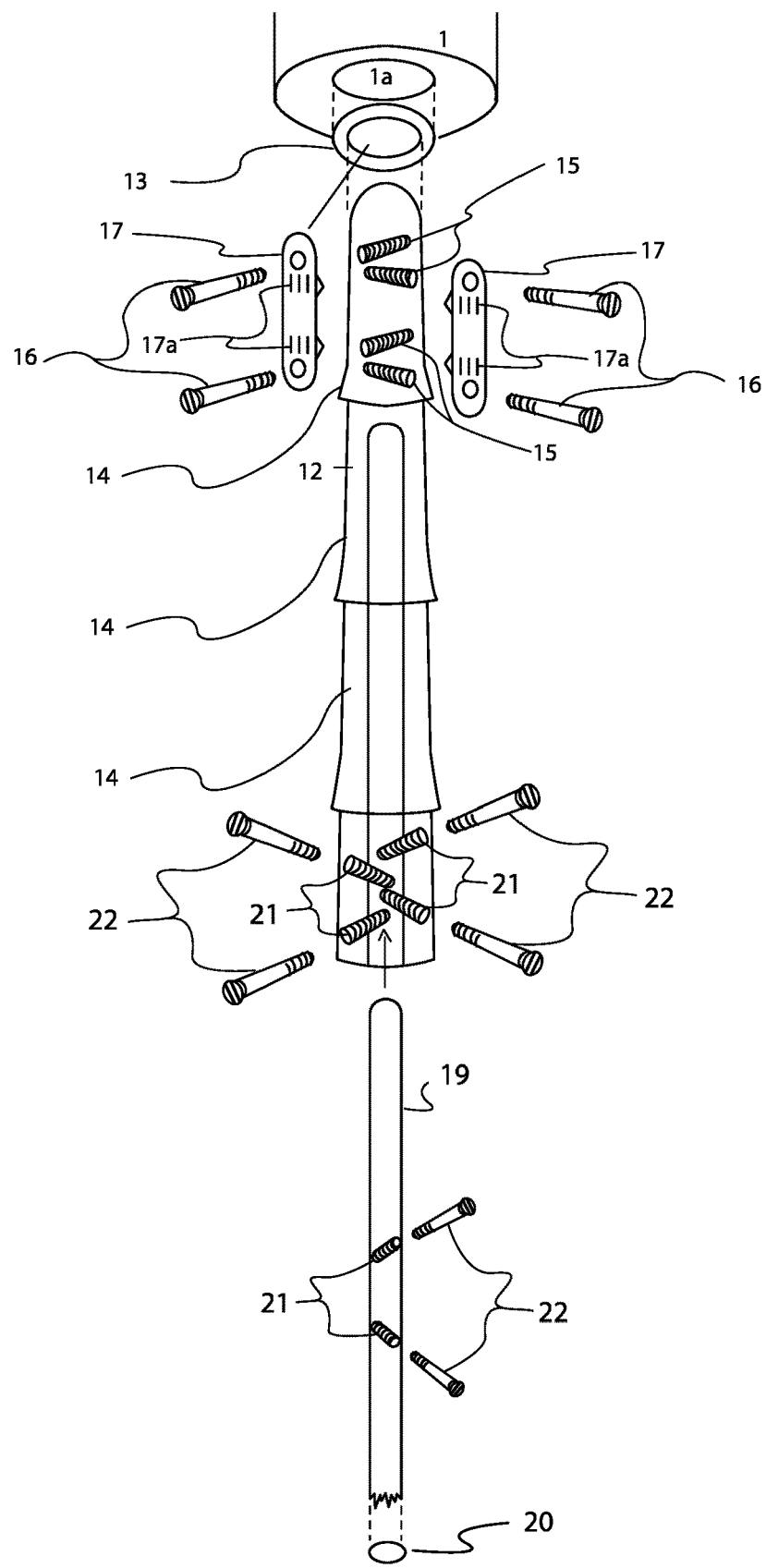
FIG. 2 is an exploded view of a portion of an embodiment of the invention of FIG. 1.

Turning to FIG. 2, most of the attachment to the axial skeleton long bone is by lengthwise long bone axial rods composed of nickel-titanium or equivalent bio-acceptable material. An embodiment includes a distal end amputation longbone 1 with prosthetic rod inserted into the long bone medullary cavity 1a. The long bone rod 12 inserts into the long bone medullary cavity 1a. The rods are substantially oblong in cross section. The oblong cross section transfers rotational forces to the long bone and keeps the implant from rotating within the long bone medullary cavity. The long bone rod is hollow for accepting the transfer rod 19.

The long bone rod has wedge-like flare-anchors 14 along the long-bone implant. The implant flare-anchors 14 support the implant against extrinsic forces that will pull at the implant, such as carrying a weight in a prosthetic forearm. Additionally, the long-bone implant has mounting bores 15 through which screws 16 attach fixation plates 17 which are external to the bone, and provide additional mounting stability against forces transmitting from the external environment to long bone of the body. The diagram shows multiple bore holes and screws, but not all will necessary be utilized at the time of implantation.

The fixation plates 17 have several rows of mounting teeth 17a to grip into the cortical bone as a structural interface. The long bone implant rod 12 is hollow and accepts an inserted internal to external (I/O) transfer rod 19. The I/O rod 19 (see FIGS. 1 and 3) is the physical connection between the long bone implant and the soft tissues of the limb. It interfaces to the soft tissues of the limb by various PEEK rings. It connects to external prosthetics by a male/female dual ratchet—socket mechanism shown as 9 and 10, respectively. The I/O rod 19 is also a substantially oblong ellipse 20 for transfer of rotation forces.

The I/O rod 19 is mounted to the distal end of the long-bone rod 12 by screw bores 21 and fixation screws 22. The diagram shows multiple bore holes and screws, but not all will necessary be utilized at the time of implantation.

Figure 3:
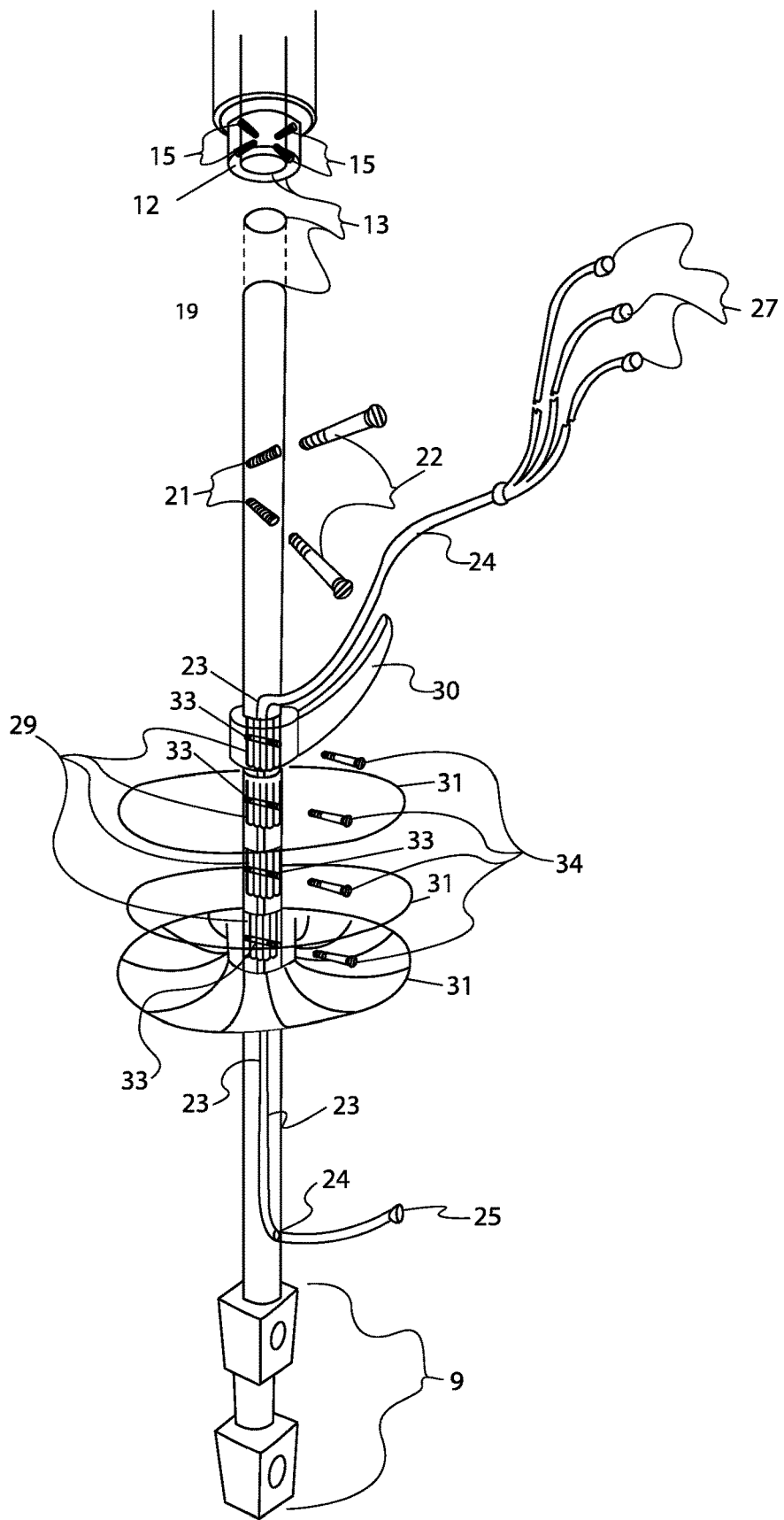
FIG. 3 is an exploded view of a portion of an embodiment of the invention of FIG. 1.

Turning to FIG. 3, "PEEK" stands for polyetheretherketone, which is a semi-crystalline, high temperature plastic. It is chosen to represent any selection of a large family of bio-neutral polymers available for surgical implantation purposes.

The long bone axial rod 12 has bore holes 15, as does the I/O transfer rod 19, through which fixation screws 22 mount. The I/O transfer rod 19 is also substantially oblong in cross section 13, to transmit rotational force along the axis of the rod-to-long-bone-implant interface.

The transfer rod 19 has a central channel 23, through which a sealed micro-wire cable 24 insulated with PEEK or other bio-acceptable dielectric material, attaches to a modified Utah Array 46, which itself interfaces to a nerve/nerve bundle. The micro wire 24 runs from inside the limb or body region nerve attachment site, then passes down through the I/O rod 19, and exits the I/O rod to the exterior of the body, where it can attach by an appropriate connector to an external processor 25.

The micro-wire cables 24 can come in bundles 27, and attach to micro connectors that clamp directly onto an associated nerve or nerve bundle (see FIG. 4). The transfer rod 19 has multiple sequential areas of gear-like ridges 29 about 1-2 cm wide, to which mating slotted rings 30 and 31 will allow full attachment to the rod for various connective purposes and at various tissue layers.

Referring to FIGS. 3, 4A-4C, and 5A-5D, in general, there is an attachment ring for any PEEK-ring to limb tissue layer attachments. Attachment rings may be for one, two, three, four or more associated muscle groups 31. There are PEEK-ring attachments for tissue closure at the fascia and dermal layers 32. Each PEEK-ring will attach by sliding into position. All PEEK rings are bore hole 33 and screw 34 mounted, or have clamped rings 36 that are bore hole/screw mounted, and closure clip retained.

At the end of the transfer rod 19, external to the limb or other bodily attachment point, is a dual ratchet type connector 9 sized for appropriate load bearing, with each ratchet dimension likely ranging from about 1 to about 2.5 cm range on each side.

There is a simple ratchet retention spring-ball system for initial connection, and between the two ratchet areas is a central rod area for a retention clip 11 to maintain definitive attachment of external prosthetic devices.

Figure 4A:
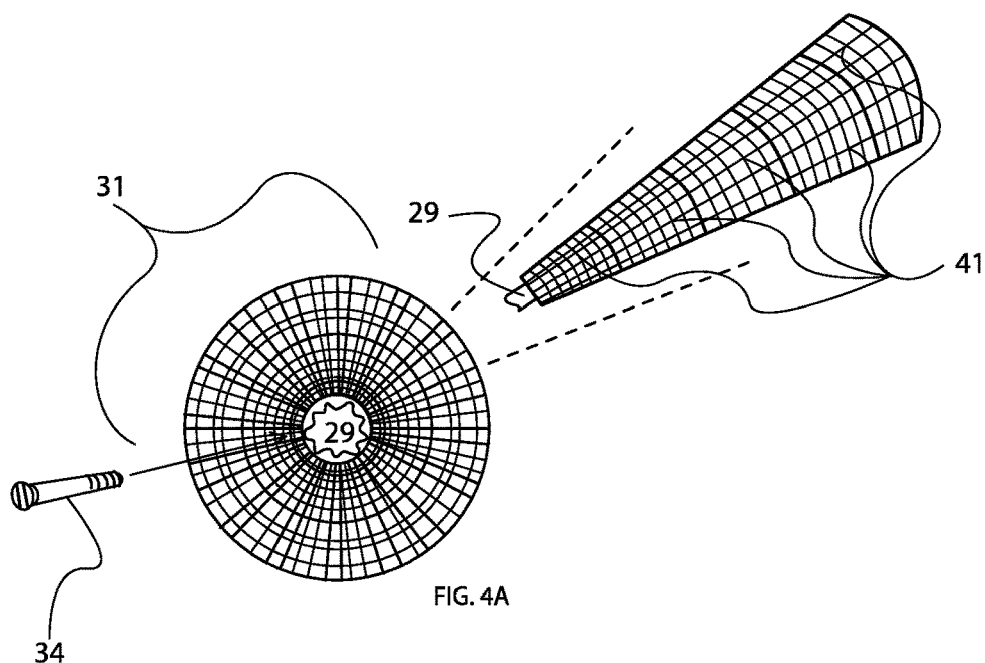
FIG. 4A is an exploded view of the attachment rings of an embodiment of the present invention.
Figure 4B:
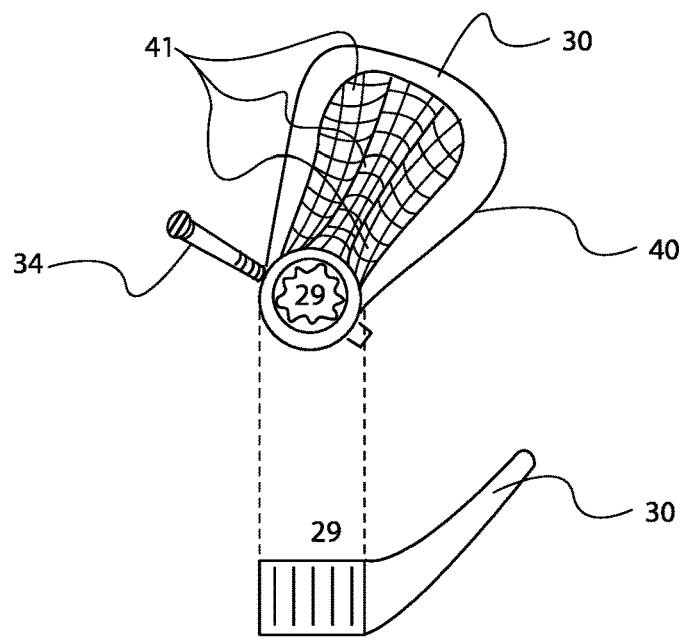
FIG. 4B is an exploded view of attachment rings of an embodiment of the present invention.
Figure 4C:
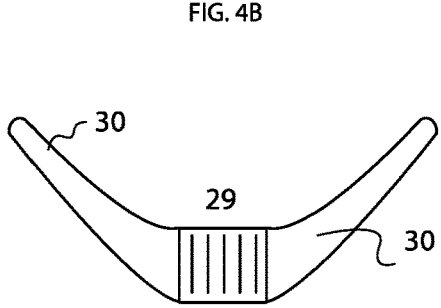
FIG. 4C is an alternative embodiment of the attachment rings of an embodiment of the present invention.
Figure 5A:
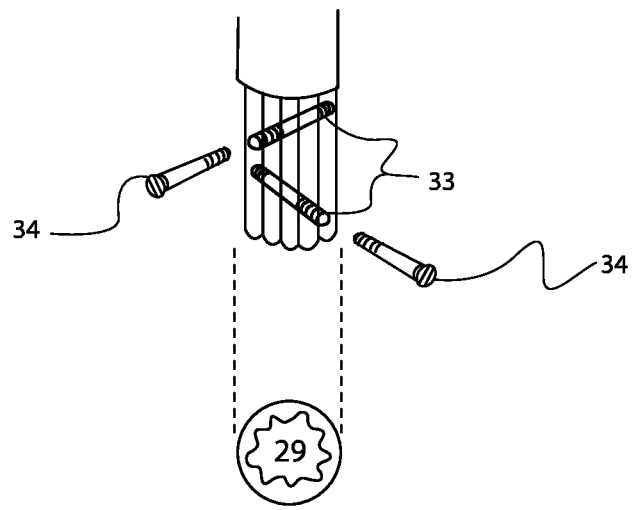
FIG. 5A is an expanded view of a portion of the attachment rings of an embodiment of the present invention.
Figure 5B:
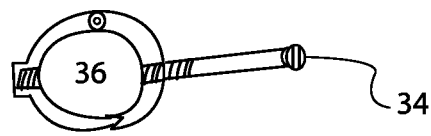
FIG. 5B is an expanded view of a portion of the attachment rings of an embodiment of the present invention.
Figure 5C:
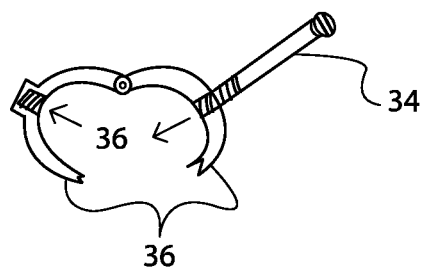
FIG. 5C is an expanded view of a portion of the attachment rings of an embodiment of the present invention.
Figure 5D:
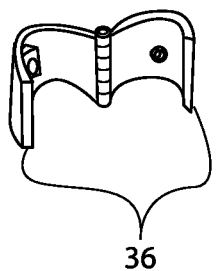
FIG. 5D is an expanded view of a portion of the attachment rings of an embodiment of the present invention.
Figure 6A:
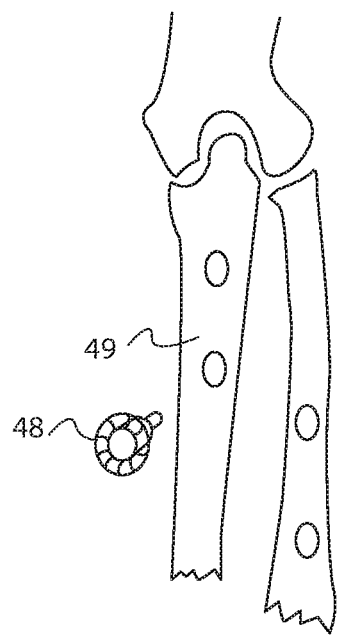
FIG. 6A is a side view of an embodiment of the present invention.
Figure 6B:
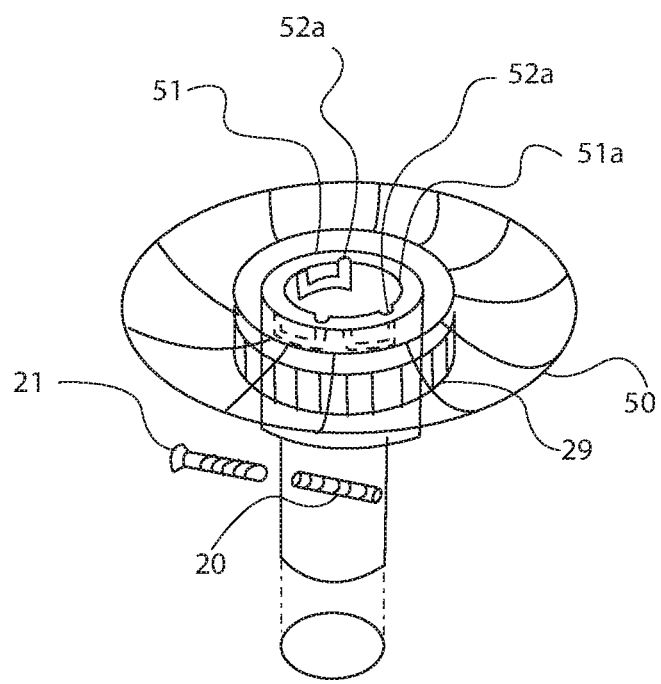
FIG. 6B is an expanded view of an embodiment of the present invention.
Figure 7:
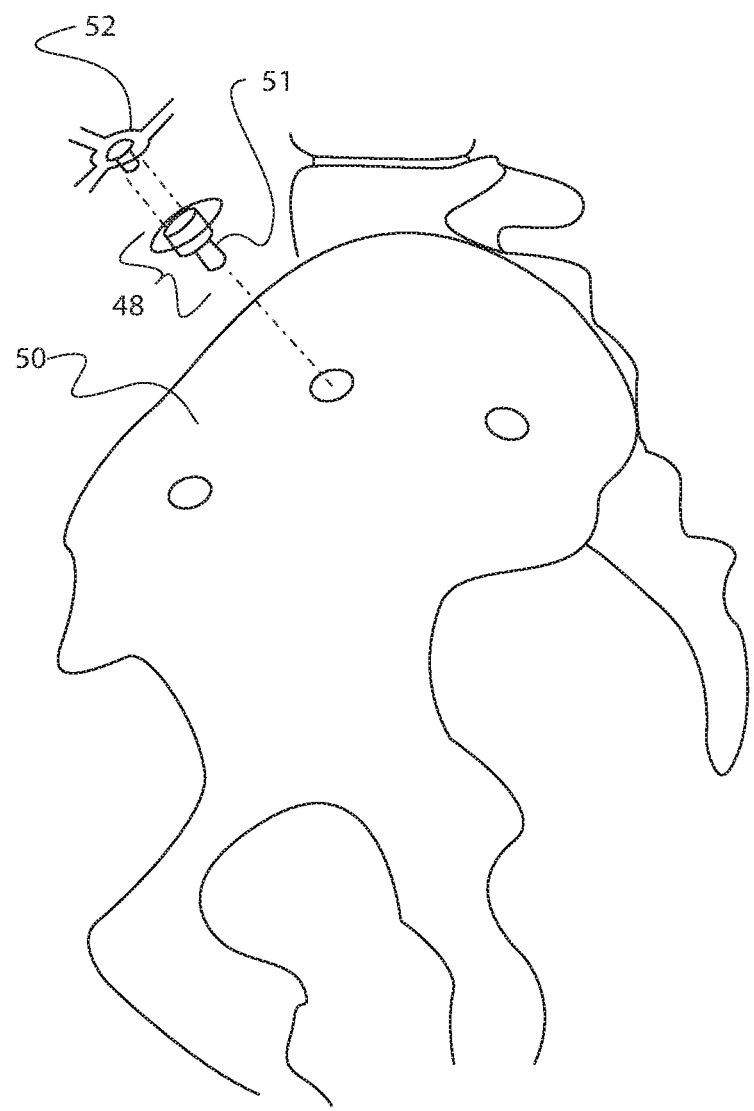
FIG. 7 is a top view of an embodiment of the present invention.
Figure 8A:
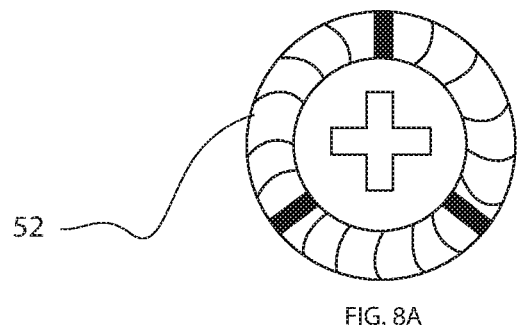
FIG. 8A is a top view of an embodiment of the present invention.
Figure 8B:
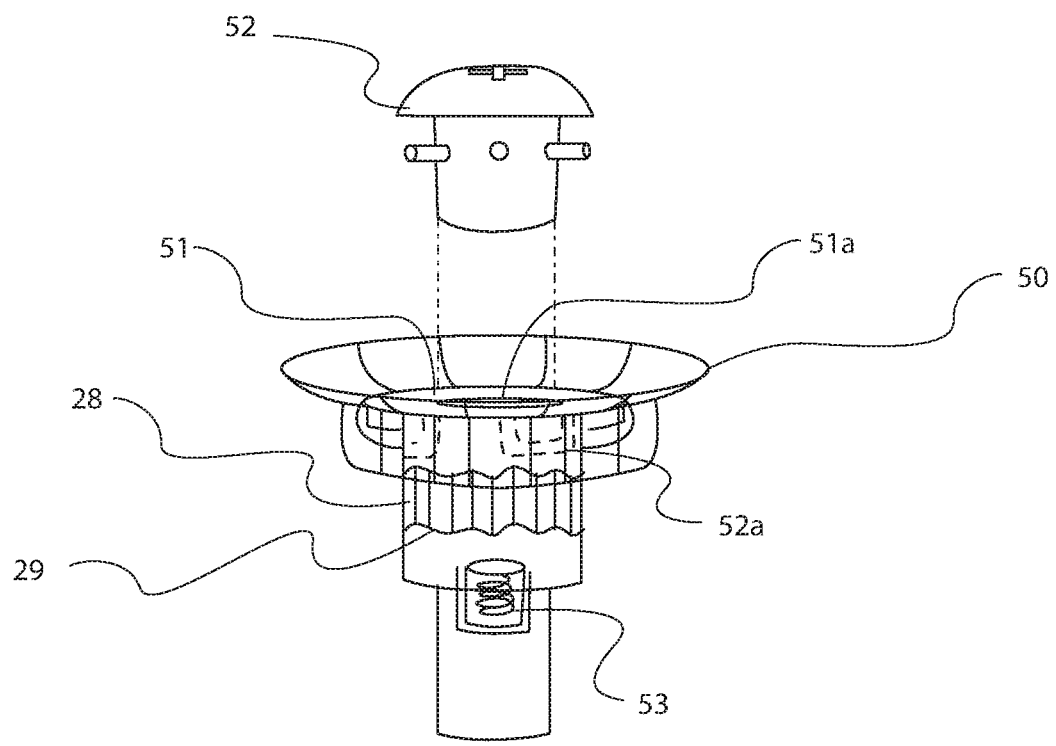
FIG. 8B is a side view of an embodiment of the present invention.
Figure 8C:
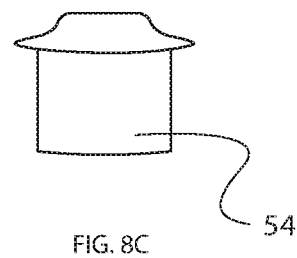
FIG. 8C is a side view of an embodiment of the present invention.

As best seen in FIGS. 4a-c, the PEEK-rings 30 and 31 attach to the transfer rod 19 at the slotted, gear-like interface area 29. The PEEK-rings that attach to muscle groups 30 has from one to four or more attachment flanges 40, designed as levers connecting between muscle/tendons and the I/O transfer rod 19. Muscle fibers 5 or tendons are surgically attached to the flanges 40 to provide intra-limb force transfer to the rod assemblies.

The PEEK-rings 31 have a metal, preferably nickel-titanium, mounting scaffold as a skeletal framework, with PEEK webbing-mesh 41 for suture and cyto-cellular attachment. The PEEK-rings for fascial and dermal attachment have a transitional web/mesh with the central area being solid PEEK with underlay of nickel-titanium scaffold. This transitions to a progressively "looser" web zone of PEEK and ends at the outer ring of metal scaffold, PEEK mesh and sub-mesh composed of collagen/allogenic hyaluronic acid (or other equivalent connective tissue biosynthetic substrate material) webbing.

It is into this PEEK/Collagen webbing which the fascia 6 or dermal 7 layers, as seen in FIG. 1 are sutured, and into which the fascia and derma will grow and interweave with for exclusion of any external environment when fully healed. Such interfaced healing may be augmented by the use of epidermal growth factors or vascular endothelial growth factors, or similar endovascular growth promoting bio-molecules.

Figure 9A:
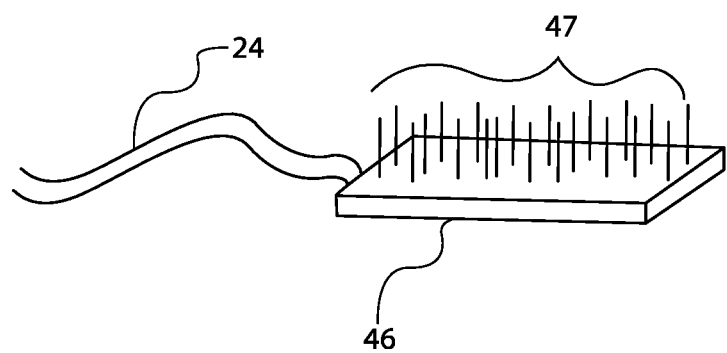
FIG. 9A is a side view of the Utah Array of an embodiment of the present invention.
Figure 9B:
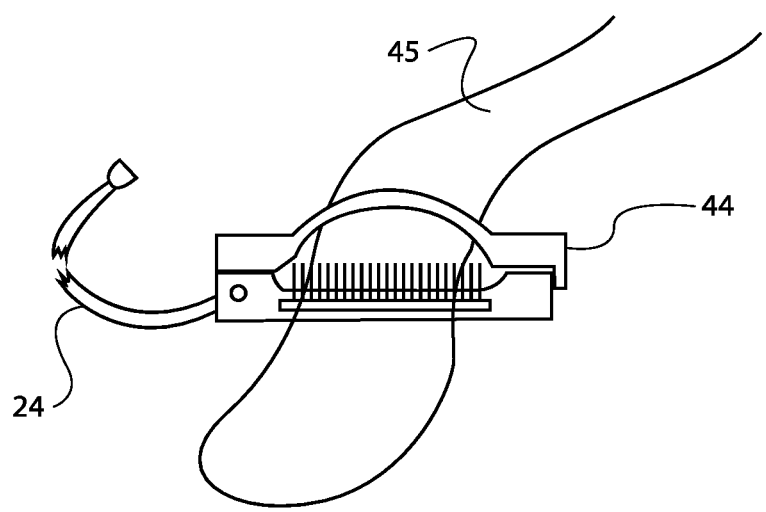
FIG. 9B is a side perspective view of a nerve clip of an embodiment of the present invention.

Referring to FIGS. 9A-9B, the micro-wire cables 24 attach to nerve/bundle clamps 44, that penetrate through each associated nerve sheath 45 into the nerve cytoplasm itself and clamp onto the nerve(s). The nerve(s) are penetrated by appropriately sized modified Utah Array (UA) carbon fiber spindles 47, which are integrated onto silicon on insulator (SOI) digital signal processor (DSP).

The SOI long dimension ranges from about 1 mm to about 5 mm, according to the size of the target nerve/bundle. The Utah Array is composed of about 100 nm diameter carbon fibers spaced about 100 nm apart, are about 5 mm to about 25 mm high, and are coated with sphingosine, or other nerve sheath cell related molecule. The carbon fiber coating allows for a more integrated transmembrane entry through the nerve sheath cell membrane and into the cellular cytoplasm.

Human nerves typically are 0.1-5 micrometers in diameter. Current generation integrated circuit transistor gate size is 14 nm. The DSP is configurable after implantation to group sets of the UA splines into functional groups and sensory or excitatory pathways.

The DSP detects the changes in the nerve cells' ion fluxes, surface potentials and internal voltages. It digitizes that information (24 bit) and serializes the information to allow connection 8 to exterior processing elements for transmission of the nerve signal data to the external environment. The nervous system connection and processing system also allows feedback signals to be returned to the nerve bundle by digital to analog processing via the same UA/DSP and potentials gated out to the UA array/nerve interface.

Referring to FIGS. 6A, 6B, 7, 8A, 8B and 8C, an additional type of prosthetic attachment 48 is shown mounted in transverse direction to a particular bone, such as the ulna (forearm) 49 or ileum (lateral pelvis) 50. These implants are meant for load bearing and external accessory attachment.

The central implant 51 has PEEK-ring zones for attachment to fascia and dermis, similar to areas 31, 40, and 41 in FIG. 4. The central mount 52 is metal, preferably nickel-titanium, and has a central channel 51a that is visible at the skin surface. A pronged-stud connector 53 fits into the channel 51a and provides mechanical connection to any mount via at least one pronged stud that inserts into locking channels 52a and turns into a locked position and is spring 54 pressure loaded into a held position.

Any attachment of appropriate size and purpose could mount to the accessory mount anchors, such as a load bearing backpack, additional attachments to a large manually operated tool, and so on.

A rubber plug 55 inserts into the empty stud central channel to keep the connector clean between uses.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the method (and components of the individual operating components of the method) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections might be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A system for attachment of a device to a bone comprising:
   a. a hollow long bone axial rod with a proximal and distal end that is configured to be inserted and secured into a long bone medullary cavity at the distal end;
   b. a transfer rod with a proximal and distal end mounted to the distal end of the long bone axial rod and a central channel extending through the transfer rod from the proximal end to the distal end;
   c. an external processor connected to the transfer rod at the distal end of the transfer rod; and
   d. a plurality of attachment rings for attaching at least one muscle group, at least one fascia layer and at least one dermal layer to the transfer rod.

2. The system of claim 1 wherein the attachment rings are constructed from a bio-neutral polymer suitable for surgical implantation of the body.

3. The system of claim 1 further comprising a transitional webbed area between the attachments rings and the fascia and dermal layers.

4. The system of claim 3 further comprising a metal mounting scaffold which forms a skeletal frame for the transitional webbed area.

5. The system of claim 4 further comprising connective tissue biosynthetic substrate material.

6. The system of claim 5 wherein the webbed area has a central area closest to the attachment ring formed from the solid bio-neutral polymer on the skeletal frame and as the webbing extends to the fascia and dermal layer the webbing is formed from progressively less bio-neutral polymer and progressively more of the connective tissue biosynthetic substrate material.

7. The system of claim 6 wherein the fascia and dermal layer interweave with the webbed area.

8. The system of claim 7 further comprising endovascular growth promoting bio-molecules wherein the endovascular growth promoting bio-molecules promote the fascia and dermal layer interweaving with the webbed area.

9. The system of claim 1 further comprising:
   a. at least one sealed micro-wire cable insulated with a bio-acceptable dielectric material with a proximal and distal end;
   b. at least one nerve bundle clip with a Utah Array of a plurality of carbon fiber spindles;
   c. at least one digital signal processor;
   d. at least one transcutaneous connector; and
   e. at least one external processor;
   wherein the nerve bundle clip clamps onto the nerve and the nerve is penetrated by the carbon fiber spindles;
   wherein the Utah Array is integrated with the digital signal processor;
   wherein the nerve bundle clip attaches to the proximal end of the micro-wire cable;
   wherein the digital signal processor is configured to collect and transmit data from the plurality of nerves to the external processor and additionally configured to transmit data from the external processor to the plurality of nerves.

10. The system of claim 9 wherein the Utah Array carbon fiber spindles are about 100 nanometers in diameter, about 5 to about 25 micrometers high, and spaced about 100 nanometers apart and are coated with a nerve sheath cell molecule material.

11. The system of claim 9 wherein the Utah Array carbon fiber spindles are grouped into sets to form splines.

12. The system of claim 11 wherein the digital signal processor groups sets of the splines into functional groups, sensory pathways or excitatory pathways.

13. The system of claim 12 further comprising an exterior processing element wherein the digital signal processor detects a nerve signal from the splines of the Utah Array; wherein the digital signal processor digitizes the nerve signal and transmits the digitized nerve signal via the micro-wire cables running through the length of the central channel of the transfer rod and through the subcutaneous connector to the exterior processing element.

14. The system of claim 12 wherein a feedback signal from the exterior processing element is returned to the nerve through the subcutaneous connector via the micro-wire cable up the length of the central channel of the transfer rod to the digital signal processor; wherein the digital signal processor converts the feedback signal from digital to analog and transmits the feedback signal to the splines of the Utah Array; and wherein the Utah Array gates the feedback signal into the nerve.

15. A system for attachment of a device to a bone comprising:

e. a device with a proximal and a distal end with two female socket connectors at the proximal end;

f. a hollow long bone axial rod with a proximal and distal end that is configured to be inserted and secured into along bone medullary cavity and the distal end; and g. a transfer rod with a proximal and distal end mounted to the distal end of the long bone axial rod at the proximal end of the transfer rod with at least two male ratchet connectors separated by a central rod portion at the distal end of the transferred;

wherein the male ratchet connectors are inserted into the female socket connectors using a ratchet retention spring ball system.

16. The system of claim 15 further comprising a retention clip that is clipped onto the central rod portion after the male ratchet connectors are inserted into the female socket connectors.

\* \* \* \* \*